United States Patent [19]

Venkatesan et al.

[11] Patent Number: 5,292,742
[45] Date of Patent: Mar. 8, 1994

[54] ANGIOTENSIN II RECEPTOR BLOCKING 2,3,6 SUBSTITUTED QUINAZOLINONES

[75] Inventors: Aranapakam M. Venkatesan, Elmhurst; Jeremy I. Levin, Nanuet, both of N.Y.

[73] Assignee: American Cyanamid Company, Wayne, N.J.

[21] Appl. No.: 52,939

[22] Filed: Apr. 23, 1993

[51] Int. Cl.$^5$ .............. A61K 31/505; C07D 403/14; C07D 403/10
[52] U.S. Cl. .............. 514/259; 544/90; 544/229; 544/284; 544/287
[58] Field of Search ............ 544/284; 514/259

[56] References Cited

U.S. PATENT DOCUMENTS 5,162,325 11/1992 Chakravarty et al. .......... 514/259
5,202,322 4/1993 Allen .......................... 514/228.2

FOREIGN PATENT DOCUMENTS 407342 1/1991 European Pat. Off. .
411766 2/1991 European Pat. Off. .
445811 9/1991 European Pat. Off. .
481448 4/1992 European Pat. Off. .
512870 11/1992 European Pat. Off. .

*Primary Examiner*—Emily Bernhardt
*Attorney, Agent, or Firm*—Thomas S. Szatkowski

[57] ABSTRACT

The invention provides novel 2,3,6-substituted quinazolinones having the formula

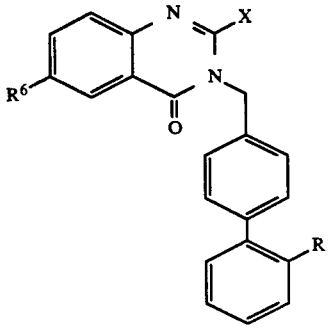

Formula I wherein X, R, $R^6$ are described in the specification which have activity as angiotensin II (AII) antagonists.

22 Claims, No Drawings

ANGIOTENSIN II RECEPTOR BLOCKING 2,3,6 SUBSTITUTED QUINAZOLINONES

BACKGROUND OF THE INVENTION

1. Field of the Invention This invention relates to certain novel 2,3,6 substituted quinazolinone compounds which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which have angiotensin II-antagonizing properties and are useful as antihypertensives:

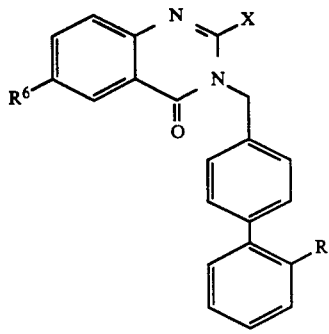

Formula I wherein:
R is

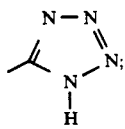

X is straight or branched alkyl of 3 to 5 carbon atoms;
$R^6$ is

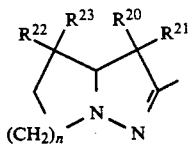

$R^{20}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{21}$ is H, straight chain lower alkyl of 1 to 4 carbon atoms, phenyl, substituted phenyl (substitution selected from mono-lower alkyl of 1 to 3 carbon atoms, trifluoromethyl, nitro, 0-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{22}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

n is 1 or 2;
and pharmaceutically acceptable salts of these compounds.

The present invention also provides novel intermediate compounds, methods for making the novel 2,3,6-substituted quinazolinone angiotension II antagonizing compounds, methods for making the novel intermediates, methods of using the novel quinazolinone angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

Referring to Scheme I, the corresponding anthranilic acid 2 where $R^{10}$ is I, is heated to reflux in alkyl acid anhydride 3 wherein X is alkyl of 3 to 5 carbon atoms to provide the 4H-3,1-benzoxain-4-ones 4 which are isolated by concentrating the reaction mixtures and used without further purification. When the 4H-3,1-benzoxazin-4-ones 4 are refluxed in ethyl alcohol containing ammonia, or ammonium hydroxide solution, the quinazolinone intermediates 5 are obtained.

Scheme I

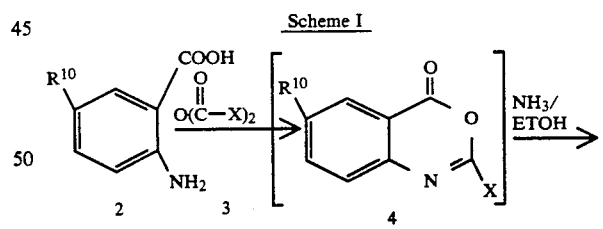

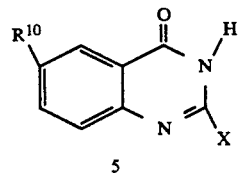

As outlined in Scheme II, quinazolinone intermediates 5 are reacted with copper(I) cyanide to give quinazolinone 6. Reaction of 6 with sodium azide in the presence of tri-n-butyltin chloride in refluxing xylene affords the desired tetrazole 7. Contemplated equivalents of tri-n-butyltin chloride include tri-(lower alkyl $C_1$-$C_4$) tin chlorides and bromides. Contemplated equivalents to sodium azide include potassium azide, cesium azide, calcium azide and lithium azide.

As illustrated in Scheme III, 7 is reacted with bromo-substituted olefin 8 where $R^{20}$, $R^{21}$, $R^{22}$, $R^{23}$ and n are hereinbefore defined to give substituted product 9. The reaction of substituted quinazolinone 9 with biphenyl 10 where $R^{18}$ is cyano prepared by the methods outlined in D. Carini, J. Med. Chem. 34, 2525–2547(1991) gives coupled product 11 by dissolving 9 and 10 in acetone or another suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium hexamethyldisilazide for 2–48 hours, at 20°–60° C. The coupled product 11 may be purified by chromatography or used as in further transormations. Heating 11 in diphenylether gives cyclized product 12.

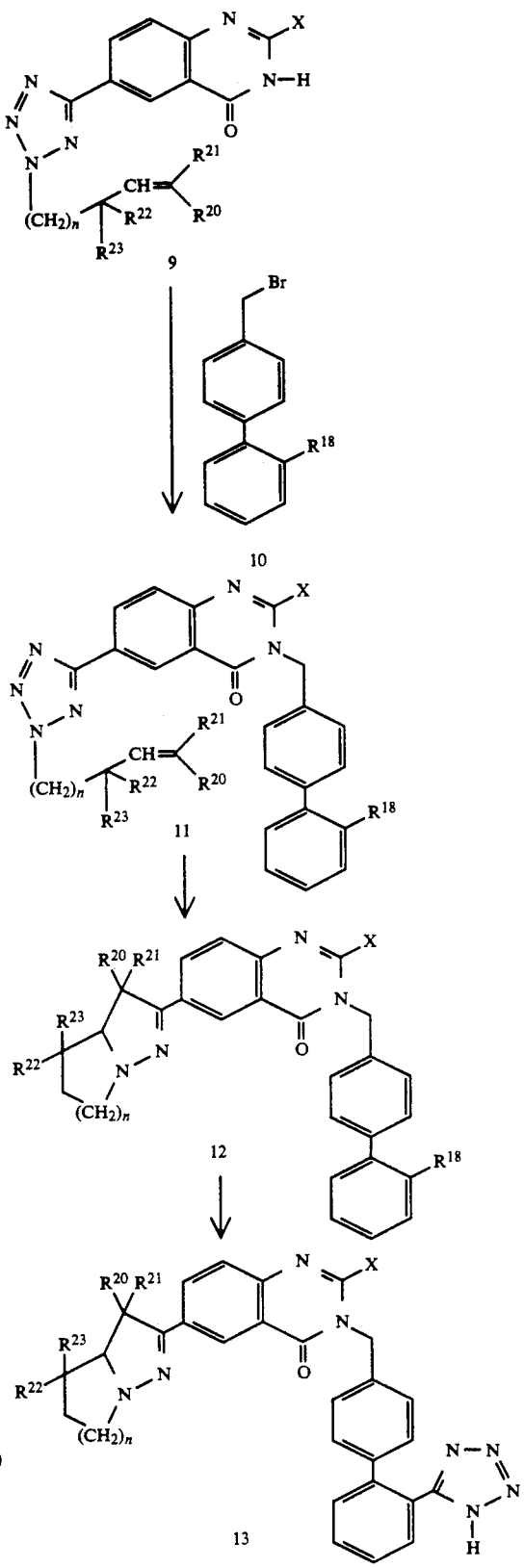

Reaction of 12 where $R^{18}$ is cyano with sodium azide in the presence of tri-n-butyltin chloride in refluxing xylene affords the desired tetrazole 13. Contemplated equivalents of tri-n-butyltin chloride include tri-(lower alkyl $C_1$-$C_4$) tin chlorides and bromides. Contemplated equivalents to sodium azide include potassium azide, cesium azide, calcium azide and lithium azide.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium, magnesium and ammonium salts.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation are illustrated by the following non-limiting examples.

EXAMPLE 1

2-Butyl-6-iodo-4(1H)-quinazolinone

To 20.0 g of 2-amino-5-iodobenzoic acid is added 75 ml of valeric anhydride. The mixture is heated at reflux for 18 hours and then concentrated under reduced pressure. The resulting residue is suspended in 200 ml of 30% ammonium hydroxide and 300 ml of ethyl alcohol. This mixture is heated at reflux for 18 hours and then allowed to cool to room temperature. After cooling, the precipitate is collected and crystallized from ethyl alcohol to give 3.22 g of the desired product as a solid, m.p. 258°-260° C.

EXAMPLE 2

2-Butyl-6-cyano-4(1-H)-quinazolinone

A mixture of 6.4 g of 2-butyl-6-iodo-4(1H)-quinazolinone in 25 ml of pyridine is added 3.6 g of copper(I) cyanide followed by heating at reflux for 16 hours. The reaction mixture is poured into water and stirred at room temperature for 8 hours. The suspension is filtered and the cake washed well with water and air dried. The solid is dissolved in 3:1 chloroform-methanol and dried with $MgSO_4$. The volatiles are evaporated in vacuo to give 3.2 g of the desired pro-duct as a solid. m.p. 243°-45° C.

EXAMPLE 3

2-Butyl-6-(1H-tetrazol-5-yl)-4(1H)-quinazolinone

A mixture of 1.1 g of 2-Butyl-6-cyano-4(1H)-quinazolinone 3.2 g of tri-n-butyltin chloride and 640 mg of sodium azide in 30 ml of toluene is heated at reflux for 48 hours. The reaction mixture is cooled to room temperature and dry HCl gas passed through the reaction mixture for 10 minutes. The reaction mixture is diluted with hexane and filtered. The residue is dried, washed with water and dried to give 1.5 g of the desired product as a solid, m.p. 225° C.

EXAMPLE 4

2-Butyl-6-[2-(4-pentenyl)-2H-tetrazol-5-yl]-4(1H)-quinazolinone

A mixture of 3.0 g of 2-butyl-6-(1H-tetrazol-5-yl)-4(1H)-quinazolinone, 2.2 g of 5-bromo-1-pentene and 2 ml of N,N-diisopropylethylamine in 50 ml of tetrahydrofuran is refluxed for 24 hours. The volatiles are evaporated in vacuo to a residue which is partitioned between chloroform and water. The organic layer is dried over $MgSO_4$, filtered and evaporated in vacuo to a residue which is purified by column chromatography on silica gel by elution with 3:2 ethyl acetate-hexanes to give a residue which crystallizes from ethyl acetate-hexanes to give 2.0 g of the desired product as a solid, m.p. 130° C.

EXAMPLE 5

2-Butyl-6-[2-(5-hexenyl-2H-tetrazin-5-yl]-4(1H)-quinazolinone

A mixture of 2.7 g of 2-butyl-6-(1H-tetrazol-5-yl)-4(1H)-quinazolinone, 3 ml of 5-bromo-1-hexene, 3 ml of diisopropylamine in 50 ml of tetrahydrofuran is refluxed for 24 hours. The volatiles are evaporated in vacuo to a residue which is partitioned between chloroform and water. The organic layer is dried over $MgSO_4$, filtered and evaporated in vacuo to a residue which is purified by column chromatography on silica gel by eluting with 3:2 ethyl acetate-hexanes to give 2.9 g of the desired product as a solid, m.p. 140° C.

EXAMPLE 6

4'-[[2-Butyl-4-oxo-6-[2-(4-pentenyl)-2H-tetrazol-5-yl]-3(4H)-quinazolinyl]methyl]-[1,1'-biphenyl]2-carbonitrile A mixture of 1.01 g of 2-butyl-6-[2-(4-pentenyl)-2H-tetrazol-5-yl]-4(1H)-quinazolinone, 1.09 g of 4'-(bromomethyl)[1,1'-biphenyl]-2-carbonitrile and 2.0 g of potassium carbonate in 100 ml of acetone is refluxed for 24 hours. The reaction mixture is filtered and the filtrate evaporated in vacuo to a residue which is purified by chromatography on silica gel by elution with 30% ethyl acetate-hexanes to give 1.5 g of the desired product as a yellow foam.

$M^+=529.6$, $M^{+1}=530$.

EXAMPLE 7

4'-[[2-Butyl-6-[1-(5-hexenyl)-1H-tetrazol-5-yl]-4-oxo-3(4H)-quinazolinyl]methyl][1,1'-biphenyl]-2-carbonitrile A mixture of 1.7 g of 2-butyl-6-[2-(4-hexenyl)-2H-tetrazol-5-yl]-4(1H)-quinazolinone, 1.9 g of 4'-(bromomethyl)[1,1'-biphenyl]-2-carbonitrile and 3.0 g of potassium carbonate in 100 ml of acetone is refluxed for 24 hours. The reaction mixture is filtered and the filtrate evaporated to a residue which is purified by chromatography on silica gel by elution with 30% ethyl acetate-hexanes to give 2.3 g of the desired product as a yellow foam.

$M^+ = 544$.

EXAMPLE 8

4'-[2-Butyl-4-oxo-6-(3a,4,5,6-tetrahydro-3H-pyrrolo[1,2-b]pyrazol-2-yl)-3(4H)-quinazolinyl][1,1'-biphenyl]-2-carbonitrile A mixture of 1.01 g of 4'-[[2-Butyl-4-oxo-6-[2-(4-pentenyl)-2H-tetrazol-5-yl]-3(4H)-quinazolinyl]-methyl]-[1,1'-biphenyl]-2-carbonitrile is suspended in 100 ml of diphenylether and heated for 3 hours. The reaction mixture is cooled to room temperature and diluted with 1L of hexanes. The oily compound is separated from the hexanes-diphenyl ether mixture and purified by column chromatography on silica gel by elution with 75% ethyl acetate-hexanes to give 2.1 g of the desired product as a yellow solid.

$M^+ = 501$.

EXAMPLE 9

4'-[[2-Butyl-6-(3,3a,4,5,6,7-hexahydro-pyrazolo-[1,5-a]pyridin-2-yl)-4-oxo-3(4H)-quinazolinyl]-methyl][1,1'-biphenyl]-2-carbonitrile A mixture of 5.43 g of 4'-[[2-butyl-6-[1-(5-hexenyl)-1H-tetrazol-5-yl]-4-oxo-3(4H)-quinazolinyl]methyl][1,1'-biphenyl]-2-carbonitrile in 100 ml of diphenylether is heated for 3 hours. The reaction mixture is cooled to room temperature and diluted with 1L of hexanes. The oily compound is separated from the hexanes-diphenylether mixture and purified by column chromatography on silica gel by eution with 75% ethyl acetate-hexanes to give 2.1 g of the desired product as solid.

$M^+515$.

EXAMPLE 10

2-Butyl-6-(3a,4,5,6-tetrahydro-3H-pyrrolo[1,2-b]pyrazol-2-yl)-3-[[2'-(1H-tetrazol-5-yl)[1,1'-biphenyl]-4-yl]methyl]-4(3H)-quinazolinone A mixture of 1.0 g of 4'-[2-butyl-4-oxo-6-(3a,4,5,6-tetrahydro-3H-pyrrolo-[1,2-b]pyrazol-2-yl)-3(4H)-quinazolinyl][1,1-biphenyl]-2-carbonitrile, 3.25 g of tri-n-butyl tin chloride and 600 mg of sodium azide in 500 ml of xylene is refluxed for 48 hours. The reaction mixture is cooled to room temperature and 5 ml of methanol added. Gaseous HCl is passed through the reaction mixture for 10 minutes and the resulting solid collected by filtration, washed with hexanes and water. The solid is purified by column chromatography on silica gel by elution with 90% ethyl acetate-10% hexanes containing 2 ml of methanol to give 600 mg of the desired product as yellow crystals, m.p. 126° C.

$M+H=545$.

EXAMPLE 11

2-Butyl-6-(3,3a,4,5,6,7-hexahydropyrazolo[1,5-a]-pyridin-2-yl)-3-[[2'-(1H-tetrazol-5-yl)[1,1'-biphenyl]-4-yl]methyl-4(3H)-quinazolinone A mixture of 2.0 g of 4'-[[2-Butyl-6-(3,3a,4,5,6,7-hexahydro-pyrazolo-[1,5-a]pyridin-2-yl)-4-oxo-3(4H)-quinazolinyl]methyl][1,1'-biphenyl]-2-carbonitrile, 6.5 g of tributyltin chloride and 1.2 g of sodium azide in 500 ml of xylene is refluxed for 48 hours. The reaction mixture is cooled to room temperature and 5 ml of methanol added followed by the addition of gaseous HCl for 10 minutes. The separated solid is filtered, washed with hexane and water then purified by column chromatography on silica gel by elution with 90% ethyl acetate-10% hexanes containing 2 ml of methanol to give 800 mg of the desired product as yellow crystals, m.p. 86°–87° C.

ANGIOTENSIN II ANTAGONISTS IN VITRO TESTS

Materials and Methods

Beef adrenals are obtained from a local slaughter house (Maxwell-Cohen). [$^{125}$I](Sar$^1$,ILe$^8$)-AngII, S.A. 2200 Ci/mmole, is purchased from Dupont (NEN®, Boston, Mass.). All unlabeled AngII analogs, Dimethylsulfoxide (DMSO), nucleotides, bovine serum albumin (BSA) are purchased from Sigma Chemical Co., St. Louis, MO U.S.A.

Preparation of Membranes

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2M sucrose. Unless otherwise indicated, all subsequent operations are done at 4° C. The tissue is homogenized in a glass homogenizer with a motor-driven teflon pestle with a clearance of 1.0 mm. The homogenate is centrifuged first at low speed (3,000 ×g) for 10 min. The resulting pellet is discarded and the supernatant fluid recentrifuged at 10,000×g for 15 minutes to give a P$_2$ pellet. This P$_2$ pellet is discarded and the liquid phase is carefully decanted off in clean centrifuge tubes and recentrifuged at high speed (100,000×g) for 60 min. The translucent final pellet is harvested and combined in a small volume (20–20.0 ml) of 50.0 mM Tris.HCl buffer, pH 7.2. A 100 ul aliquot is withdrawn and the protein content of the preparation is determined by the Lowry's method (Lowry, O.H., Rosebrough, N.F., Farr, A.L. and Randall, R.J., Protein measurement with Folin phenol reagent. J. Biol. Chem., 48, 265-275, 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at −70° C. until use in the binding assays.

Receptor Binding Assay

Binding of[$^{125}$I](Sar$^1$,Ile$^8$)AngII

The binding of [$^{125}$I](Sar$^1$,Ile$^8$)ANGII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I](Sar$^1$,Ile$^8$)AngII (Specific Activity, 2200 Ci/m-mole). Non-specific binding is measured in the presence of 1.0 uM unlabeled (Sar$^1$,Ile$^8$)AngII, added in 20 ul volume. Specific binding for [$^{125}$I](Sar$^1$,Ile$^8$) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [$^{125}$I](Sar$^1$,Ile$^8$) AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, Md., U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduces the radioactivity retained by the filter blanks. This method is routinely used. The filters are removed from the filter grid and counted in a Parkard ® Cobra Gamma Counter for 1 min. (Packard Instrument Co., Downers Grove, Ill., U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 μM are considered active compounds and are then evaluated in concentration-response experiments to determine their IC$_{50}$ values. The results are shown in Table I.

TABLE I

| Ex. No. | R$^6$ | X | Angiotensin II Receptor Binding IC$_{50}$ (M) |
|---|---|---|---|
| 10 | (pyrrolidinyl) | —(CH$_2$)$_3$CH$_3$ | $1.02 \times 10^{-7}$ |
| 11 | (hexahydroindazolyl) | —(CH$_2$)$_3$CH$_3$ | $5.64 \times 10^{-8}$ |

As can be seen from Table I, the compounds demonstrate excellent Angiotensin II Receptor Binding activity.

The enzyme renin acts on a blood plasma α$_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

The compounds of this invention inhibit the action of AII. By administering a compound of this invention to a rat, and then challenging with angiotensin II, a blockage of the vasopressor response is realized. The results of this test on representative compounds of this invention are shown in Table II.

AII CHALLENGE

Conscious Male Okamoto-Aoki SHR, 16–20 weeks old, weighing approximately 330 g are purchased from Charles River Labs (Wilmington, Mass.). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10-20 tubing (fused together by heat) is passed into the lower abdominal aorta and vena cava, respectively. The cannula is secured, heparinized (1,000 I.U./ml), sealed and the wound is closed. The animals are placed in plastio restraininq cages in an upright position. The cannula is attached to a Statham P23Db pressure transducer,and pulsatile blood pressure is recorded to 10–15 minutes with a Gould Brush recorder. (Chan et al., Drug Development Res., 18:75-94, 1989.)

Angiotensin II (human sequence, Sigma Chem. Co., St. Louis, Mo.) of 0.05 and 0.1 mcg/kg i.v. is injected into all rats (predosing response). Then a test compound, vehicle or a known angiotensin II antagonist is administered i.v., i.p. or orally to each set of rats. The two doses of angiotensin II are given to each rat again at 30, 60, 90, 120, 180, 240 and 300 minutes post dosing the compound or vehicle. The vasopressor response of angiotensin II is measured for the increase in systolic blood pressure in mmHg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 235 | 280 | 45 | 35 | |
| | | | | 250 | 275 | 25 | | |
| | | 0.1 | | 225 | 285 | 60 | 50 | |
| | | | | 235 | 275 | 40 | | |
| Ex. No. 10 | 3 IV | 0.05 | 30 | 230 | 242 | 12 | 13.5 | 61 |
| | | | | 240 | 255 | 15 | | |
| | | 0.1 | | 230 | 250 | 20 | 22.5 | 55 |
| | | | | 235 | 260 | 25 | | |
| | | 0.05 | 60 | 225 | 255 | 30 | 32.5 | 7 |
| | | | | 235 | 270 | 35 | | |
| | | 0.1 | | 230 | 255 | 25 | 22.5 | 55 |
| | | | | 240 | 260 | 20 | | |
| | | 0.05 | 90 | 225 | 255 | 30 | 20 | 43 |
| | | | | 240 | 250 | 10 | | |
| | | 0.1 | | 240 | 265 | 25 | 25 | 50 |
| | | | | 235 | 260 | 25 | | |
| | | 0.05 | 120 | 225 | 250 | 25 | 20 | 43 |
| | | | | 215 | 230 | 15 | | |
| | | 0.1 | | 235 | 265 | 30 | 25 | 50 |
| | | | | 220 | 240 | 20 | | |
| | | 0.05 | 180 | 210 | 235 | 25 | 22.5 | 36 |
| | | | | 215 | 235 | 20 | | |
| | | 0.1 | | 215 | 245 | 30 | 27.5 | 45 |
| | | | | 225 | 250 | 25 | | |
| | | 0.05 | 240 | 210 | 230 | 20 | 17.5 | 50 |
| | | | | 220 | 235 | 15 | | |
| SPONTANEOUSLY HYPERTENSIVE RATS n = 2 Body weights(s): 405, 400 grams | | | | | | | | |
| | | 0.1 | | 225 | 250 | 25 | 25 | 50 |
| | | | | 215 | 240 | 25 | | |
| | | 0.05 | 300 | 215 | 250 | 35 | 32.5 | 7 |
| | | | | 215 | 245 | 30 | | |
| | | 0.1 | | 210 | 255 | 45 | 35 | 30 |
| | | | | 225 | 250 | 25 | | |
| CONTROL | | 0.05 | 0 | 240 | 275 | 35 | 42.5 | |
| | | | | 245 | 295 | 50 | | |
| | | 0.1 | | 225 | 285 | 60 | 47.5 | |
| | | | | 235 | 270 | 35 | | |
| Ex. No. 11 | 3 IV | 0.05 | 30 | 230 | 240 | 10 | 7.5 | 82 |
| | | | | 220 | 225 | 5 | | |
| | | 0.1 | | 225 | 245 | 20 | 17.5 | 63 |
| | | | | 225 | 240 | 15 | | |
| | | 0.05 | 60 | 210 | 230 | 20 | 17.5 | 59 |
| | | | | 215 | 230 | 15 | | |
| | | 0.1 | | 200 | 230 | 30 | 27.5 | 42 |
| | | | | 225 | 250 | 25 | | |
| | | 0.05 | 90 | 200 | 215 | 15 | 15 | 65 |
| | | | | 210 | 225 | 15 | | |
| | | 0.1 | | 205 | 235 | 30 | 30 | 37 |
| | | | | 210 | 240 | 30 | | |
| | | 0.05 | 120 | 205 | 225 | 20 | 17.5 | 59 |
| | | | | 210 | 225 | 15 | | |
| | | 0.1 | | 200 | 230 | 30 | 27.5 | 42 |
| | | | | 210 | 235 | 25 | | |
| | | 0.05 | 180 | 210 | 230 | 20 | 17.5 | 59 |
| | | | | 210 | 225 | 15 | | |
| | | 0.1 | | 215 | 240 | 25 | 30 | 37 |
| | | | | 215 | 250 | 35 | | |
| | | 0.05 | 240 | 210 | 235 | 25 | 20 | 53 |
| | | | | 205 | 220 | 15 | | |
| | | 0.1 | | 225 | 245 | 20 | 25 | 47 |
| | | | | 210 | 240 | 30 | | |
| | | 0.05 | 300 | 215 | 240 | 25 | 25 | 41 |
| | | | | 205 | 230 | 25 | | |
| | | 0.1 | | 225 | 245 | 20 | 27.5 | 42 |
| | | | | 210 | 245 | 35 | | |

SPONTANEOUSLY HYPERTENSIVE RATS n = 2 Body weights(s): 415, 415 grams

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. for example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. A quinazolinone compound having the formula:

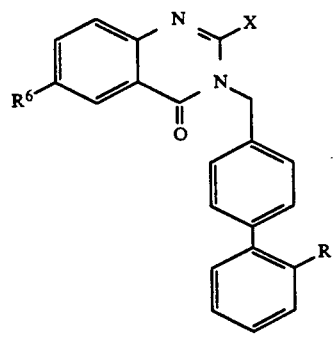

wherein
R is

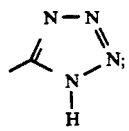

X is a straight or branched alkyl of 3 to 5 carbon atoms;
$R^6$ is

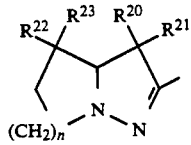

$R^{20}$ is H, straight chain lower alkyl of 1 to 4 carbon atoms, phenyl, substituted phenyl (substitution selected from mono-lower alkyl of 1 to 3 carbon atoms, trifluoromethyl, nitro, 0-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{21}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{22}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

n is 1 or 2;
or pharmaceutically acceptable salts of these compounds.

2. The compound according to claim 1 wherein said salts are selected from potassium, sodium, calcium, magnesium or ammonium.

3. The compound according to claim 1 wherein X is a straight chain alkyl of 3 to 4 carbon atoms;
$R^6$ is

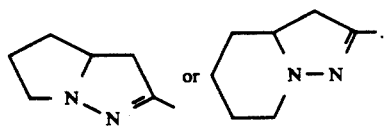

4. A quinazolinone compound having the formula:

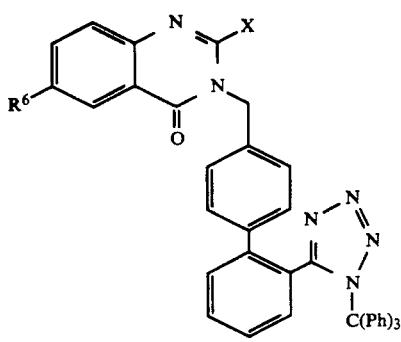

wherein:
X is straight or branched alkyl of 3 to 5 carbon atoms;
$R^6$ is

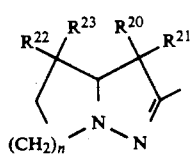

$R^{20}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{21}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{22}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

n is 1 or 2.

5. The compound according to claim 4 wherein X is a straight chain alkyl of 3 or 4 carbon atoms;
$R^6$ is

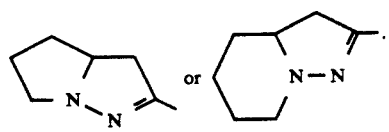

6. A quinazolinone compound having the formula:

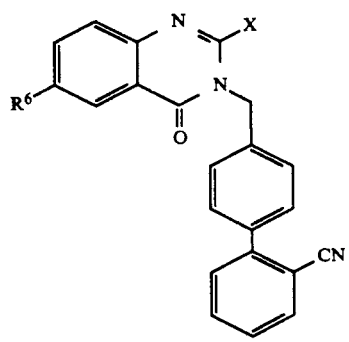

wherein:
X is straight or branched alkyl of 3 to 5 carbon atoms;
$R^6$ is

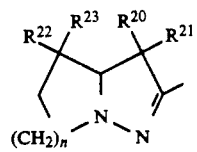

$R^{20}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{21}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

$R^{22}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

n is 1 or 2.

7. The compound according to claim 6 wherein X is a straight chain alkyl of 3 or 4 carbon atoms; R$^6$ is

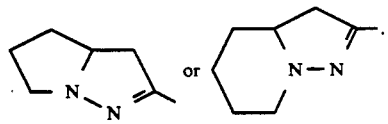

8. A quinazolinone compound having the formula:

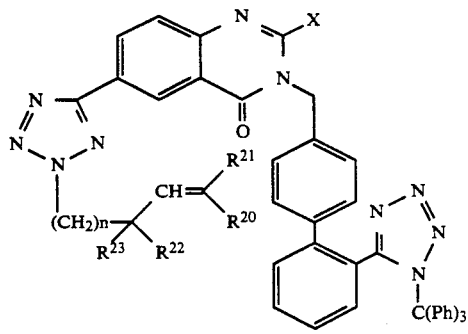

wherein:
X is a straight or branched alkyl of 3 to 5 carbon atoms;

R$^{20}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{21}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{22}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

n is 1 or 2.

9. A quinazolinone compound having the formula:

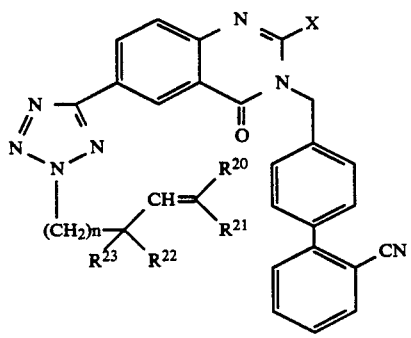

wherein:
X is a straight or branched alkyl of 3 to 5 carbon atoms;

R$^{20}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{21}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{22}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

R$^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);

n is 1 or 2.

10. A quinazolinone compound having the formula:

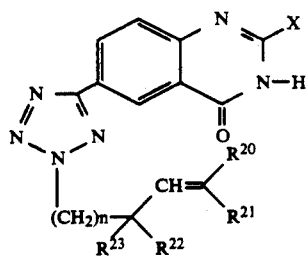

wherein:
- X is a straight or branched alkyl of 3 to 5 carbon atoms;
- $R^{20}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);
- $R^{21}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);
- $R^{22}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);
- $R^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);
- n is 1 or 2.

11. A quinazolinone compound having the formula:

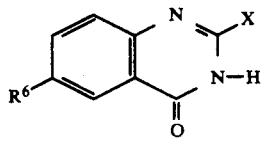

wherein:
- X is a straight or branched alkyl of 3 to 5 carbon atoms;
- $R^6$ is

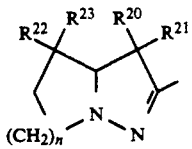

- $R^{20}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);
- $R^{21}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);
- $R^{22}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);
- $R^{23}$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms), benzyl, substituted benzyl (substitution selected from mono-lower alkyl of 1 to 3 carbon atoms, trifluoromethyl, nitro, O-alkyl of 1 to 3 carbon atoms);
- n is 1 or 2.

12. The compound according to claim 11 wherein X is a straight chain alkyl of 3 or 4 carbon atoms; $R^6$ is

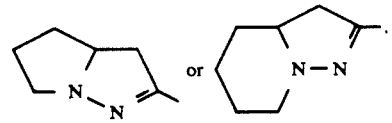

13. The compound according to claim 1 2-butyl-6-(3a,4,5,6-tetrahydro-3H-pyrrolo[1,2-b]-pyrazol-2-yl)-3-[[2'-(1H-tetrazol-5-yl)[1,1'-biphenyl]-4-yl]methyl]-4(3H)-quinazolinone.

14. The compound according to claim 1 2-butyl-6-(3,3a,4,5,6,7-hexahydropyrazolo[1,5-a]-pyridin-2-yl)-3-[[2'-(1H-tetrazol-5-yl)[1,1'-biphenyl]-4-yl]methyl-4(3H)-quinazolinone.

15. The compound according to claim 6 4'-[[2-butyl-6-(3,3a,4,5,6,7-hexahydro-pyrazolo-[1,5-a]pyridin-2-yl)-4-oxo-3(4H)-quinazolinyl]-methyl][1,1'-biphenyl]-2-carbonitrile.

16. The compound according to claim 6 4'-[2-butyl-4-oxo-6-(3a,4,5,6-tetrahydro-3H-pyrrolo[1,2-b]pyrazol-2-yl)-3(4H)-quinazolinyl][1,1-biphenyl]-2-carbonitrile.

17. The compound according to claim 9 4'-[[2-butyl-4-oxo-6-[2-(4-pentenyl)-2H-tetrazol-5-yl]-3(4H)-quinazolinyl]methyl]-[1,1'-biphenyl]-2-carbonitrile.

18. The compound according to claim 10 2butyl-6-[2-(4-pentenyl)-2H)-tetrazol-5-yl]-4(1H)-quinazolinone.

19. A pharmaceutical composition useful for treating angiotensin induced hypertension or congestive heart failure in a mammal comprising a suitable pharmaceutical carrier and an effective amount of a compound of claim 1.

20. A method of treating angiotensin induced hypertension in a mammal comprising administering a compound of claim 1 to said mammal an amount effective to lower angiotensin induced hypertension.

21. A method of treating congestive heart failure in a mammal comprising administering a compound of claim 1 to said mammal in an amount effective to treat congestive heart failure.

22. A method antagonizing the effects of angiotensin II in a mammal comprising administering a compound of claim 1 to said mammal in an amount effective to treat the effects of angiotensin II.

* * * * *